United States Patent
Kleideiter et al.

(10) Patent No.: US 10,022,353 B2
(45) Date of Patent: Jul. 17, 2018

(54) CEBRANOPADOL FOR TREATING PAIN IN SUBJECTS WITH IMPAIRED HEPATIC AND/OR IMPAIRED RENAL FUNCTION

(71) Applicant: Gruenenthal GmbH, Aachen (DE)

(72) Inventors: Elke Kleideiter, Aachen (DE); Annette Christoph, Aachen (DE); Rene Fussen, Wuerselen (DE); Joachim Ossig, Stolberg (DE); Ramesh Boinpally, Princeton, NJ (US)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 15/545,553

(22) PCT Filed: Jan. 22, 2016

(86) PCT No.: PCT/EP2016/000114
§ 371 (c)(1),
(2) Date: Jul. 21, 2017

(87) PCT Pub. No.: WO2016/116280
PCT Pub. Date: Jul. 28, 2016

(65) Prior Publication Data
US 2018/0008576 A1    Jan. 11, 2018

Related U.S. Application Data

(60) Provisional application No. 62/106,845, filed on Jan. 23, 2015.

(51) Int. Cl.
*A61K 31/407*  (2006.01)
*A61K 9/00*  (2006.01)

(52) U.S. Cl.
CPC .......... *A61K 31/407* (2013.01); *A61K 9/0053* (2013.01)

(58) Field of Classification Search
CPC ........................... A61K 31/407; A61K 9/0053
USPC ....................................................... 548/407
See application file for complete search history.

(56) References Cited

U.S. PATENT DOCUMENTS

2006/0004034 A1   1/2006  Hinze et al.
2008/0125475 A1   5/2008  Linz et al.
2008/0221141 A1   9/2008  Friderichs et al.

FOREIGN PATENT DOCUMENTS

| WO | WO 2004/043967 A1 | 5/2004 |
|---|---|---|
| WO | WO 2006/108565 A1 | 10/2006 |
| WO | WO 2008/040481 A1 | 4/2008 |
| WO | WO 2012/016695 A2 | 2/2012 |
| WO | WO 2012/016697 A2 | 2/2012 |
| WO | WO 2012/016698 A2 | 2/2012 |
| WO | WO 2012/016699 A2 | 2/2012 |
| WO | WO 2012/016703 A2 | 2/2012 |
| WO | WO 2013/007361 A1 | 1/2013 |
| WO | WO 2013/087591 A1 | 6/2013 |
| WO | WO 2013/113690 A1 | 8/2013 |
| WO | WO 2013/113857 A1 | 8/2013 |
| WO | WO 2013/170965 A1 | 11/2013 |
| WO | WO 2013/170966 A1 | 11/2013 |
| WO | WO 2013/170967 A1 | 11/2013 |
| WO | WO 2013/170968 A1 | 11/2013 |
| WO | WO 2013/170969 A1 | 11/2013 |
| WO | WO 2013/170970 A1 | 11/2013 |
| WO | WO 2013/170971 A1 | 11/2013 |
| WO | WO 2013/170972 A1 | 11/2013 |

OTHER PUBLICATIONS

International Search Report (PCT/ISA/210) issued in PCT Application No. PCT/EP2016/000114 dated Apr. 18, 2016 (four (4) pages).
Written Opinion (PCT/ISA/237) issued in PCT Application No. PCT/EP2016/000114 dated Apr. 18, 2016 (five (5) pages).
EMEA Guideline, "Guideline on the Evaluation of the Pharmacokinetics of Medicinal Products in Patients with Impaired Hepatic Function," Feb. 17, 2005, CPMP/EWP/2339/02, ten (10) pages.
FDA Guidance, "Guidance for Industry—Pharmacokinetics in Patients with Impaired Hepatic Function: Study Design, Data Analysis, and Impact of Dosing and Labeling," May 2003, U.S. Department of Health and Human Services, FDA/CDER/CBER, Clinical Pharmacology, nineteen (19) pages.
R.K. Verbeeck, "Pharmacokinetics and Dosage Adjustment in Patients with Hepatic Disfunction," Eur J Clin Pharmacol, 2008, 64(12), pp. 1147-1161.
P. Niscola et al., "Opioid Analgesics in Patients with Chronic Renal Failure: Principles for Use and Current Guidelines," G Ital Nefrol. 2011, 28(3), pp. 269-277.
P. Pham et al., "Pain Management in Patients with Chronic Kidney Disease," NDT Plus 2009, 2, pp. 111-118.
K. Linz et al., "Cebranopadol: A Novel Potent Analgesic Nociceptin/Orphanin FQ Peptide and Opioid Receptor Agonist," J Pharmacol Exp Ther. Jun. 2014, 349(3), pp. 535-548.
S. Schunk et al, "Discovery of a Potent Analgesic NOP and Opioid Receptor Agonist: Cebranopadol," ACS Medicinal Chemistry Letters, vol. 5, No. 8, Aug. 14, 2014, pp. 857-862, XP055262358.

(Continued)

*Primary Examiner* — Kristin A Vajda
(74) *Attorney, Agent, or Firm* — Norris McLaughlin & Marcus, P.A.

(57) ABSTRACT

The invention relates to Cebranopadol or a physiologically acceptable salt thereof for use in the treatment or the prevention of pain and/or opioid drug dependence in a subject with impaired hepatic and/or renal function.

15 Claims, No Drawings

(56) References Cited

OTHER PUBLICATIONS

E. Adeghate et al, "Evaluating the Phase II drugs currently under investigation for diabetic neuropathy," Expert Opinion on Investigational Drugs, vol. 24, No. 1, Aug. 29, 2014, pp. 1-15, XP055262367.
FDA Guidance, "Guidance for Industry—Pharmacokinetics in Patients with Impaired Renal Function: Study Design, Data Analysis, and Impact of Dosing and Labeling," Mar. 2010, (Revision 1), U.S. Department of Health and Human Services, FDA/CDER/CBER, Clinical Pharmacology, twenty-one (21) pages.
Annette Christoph et al., "Cebranopadol, a novel first-in-class analgesic drug candidate : first experience in patients with chronic low back pain in a randomized clinical trial", PAN Research Paper, www.painjournalonline.com, Sep. 2017, vol. 158, No. 9, pp. 1813-1824.
Elke Kleideiter et al., "Clinical Pharmacokinetic Characteristcs of Cebranopadol, a Novel First-in-Class Analgesic", Clin Pharmacokinet, 2018, vol. 57, pp. 31-50.
Qianwei Shen, "Cebranopadol, a Mixed Opiod Agonist, Reduces Cocaine Self-administration through Nociceptin Opioid and Mu Opioid Receptors", Frontiers in Psychiatry, Nov. 2017, vol. 8, Article 234, pp. 1-9.

CEBRANOPADOL FOR TREATING PAIN IN SUBJECTS WITH IMPAIRED HEPATIC AND/OR IMPAIRED RENAL FUNCTION

The invention relates to Cebranopadol or a physiologically acceptable salt thereof for use in the treatment or the prevention of pain and/or opioid drug dependence in a subject with impaired hepatic and/or renal function.

Subjects suffering from moderate to severe pain or opioid drug dependence may have impaired hepatic and/or renal function for various reasons such as genetic disposition, acquired liver and/or kidney disease, or side effect of a medication that is administered for treating another primary disorder or disease or the same disorder or disease. For example, it is known that NSAIDs may cause renal impairment.

Liver function tests are routinely performed and give information about the state of a subject's liver. Results of hepatic tests may be associated with cellular integrity, functionality, and conditions linked to the biliary tract. These tests can be used to detect the presence of liver disease, distinguish among different types of liver disorders, gauge the extent of known liver damage, and follow the response to treatment. Hepatic insufficiency can be quantified using any of a number of scales including a model end stage liver disease (MELD) score, a Child-Pugh score, or a Conn score. The Child-Pugh score employs two clinical features (encephalopathy and ascites) and three laboratory-based parameters (S-albumin, S-bilirubin and prothrombin time). Each measure is scored with 1 to 3 points, with 3 points indicating most severe derangement. The points for all five items are added and liver function is then classified into Child-Pugh classes A to C.

Similarly, kidney function tests are routinely performed and give information about the state of a subject's kidneys. Renal failure is a medical condition in which the kidneys fail to adequately filter waste products from the blood. Renal failure is mainly determined by a decrease in glomerular filtration rate (GFR), the rate at which blood is filtered in the glomeruli of the kidney. This is detected by a decrease in or absence of urine production or determination of waste products (e.g. creatinine) in the blood. GFR can be calculated from creatinine concentration in blood, creatinine concentration in urine, and volume of urine collected over 24 hours. However, in clinical practice, estimates of creatinine clearance based on the serum creatinine level are routinely used to measure GFR (eGFR) according to various formulas.

Current treatment of moderate to severe pain often involves administration of analgesics such as opioids (e.g. Tilidine, Oxymorphone), of tricyclic antidepressants such as Amitriptyline, of serotonin-norepinephrine reuptake inhibitors such as Duloxetine, of anticonvulsants such as Pregabalin, or of drugs belonging to other classes. Current treatment of opioid drug dependence typically involves administration of Methadone or Buprenorphine.

Many of these drugs, however, must not be administered to or are not recommended for subjects with impaired hepatic or renal function or at least require specific attention and care during treatment.

The liver plays a central role in the pharmacokinetics of the majority of drugs. Liver dysfunction may not only reduce the blood/plasma clearance of drugs eliminated by hepatic metabolism or biliary excretion, it can also affect plasma protein binding, which in turn could influence the processes of distribution and elimination. Portal-systemic shunting, which is common in advanced liver cirrhosis, may substantially decrease the presystemic elimination (i.e., first-pass effect) of high extraction drugs following their oral administration, thus leading to a significant increase in the extent of absorption. Chronic liver diseases are associated with variable and non-uniform reductions in drug-metabolizing activities. Subjects with liver cirrhosis are more sensitive to the central adverse effects of opioid analgesics (R. K. Verbeeck, Eur J Clin Pharmacol. 2008, 64(12), 1147-61).

In subjects with renal impairment dose adjustment is often necessary for drugs eliminated by renal excretion. The treatment of pain in subjects with impaired renal or hepatic function may also be problematic. In the presence of renal failure, significant changes occur in the metabolism and pharmacokinetics of these drugs, which can lead to adverse reactions due to the accumulation of parental compounds and active or toxic metabolites (P. Niscola et al., G Ital Nefrol. 2011, 28(3), 269-77).

The majority of opioids recommended for both moderate and severe pain undergo hepatic biotransformation and renal excretion of the parent drug and/or metabolites as the primary route of elimination. The significant renal retention of active or toxic metabolites of commonly used opioids including, but not limited to, morphine, oxycodone and propoxyphene can occur among advanced chronic kidney disease (CKD) subjects and lead to profound central nervous system and respiratory depression and hypotension. In addition, myoclonus and seizures are well-recognized serious neurological complications with the use of high doses of morphine, hydromorphone, meperidine, fentanyl and diamorphine. Dose reduction for most opioids in subjects with reduced renal function must therefore be considered to avoid drug accumulation and associated complications (P-Ch. T. Pham et al., NDT Plus 2009, 2, 111-118).

According to the information provided for commercial Amitriptyline and for commercial Oxymorphone, a reduction of dose is necessary when treating subjects with impaired renal or hepatic function in order to minimize health risk. Similarly, according to the information provided for commercial Hydrocodone dose reduction is indicated in subjects with renal impairment and severe hepatic impairment, whereas Duloxetine is contra-indicated in hepatic and severe renal impairment. It has also been reported that Pregabalin and Gabapentin require dose adaptation in subjects with renal impairment.

In other cases, when the active substance is generated in vivo upon metabolization, impaired hepatic function may result in a loss of therapeutic effect. For example, according to the information provided for commercial Tilidine, analgesic treatment in subjects with impaired hepatic function may be ineffective, as little or no Nortilidine is formed as active metabolite.

In consequence, pain therapy in subjects with hepatic or renal impairment is often difficult and conventional analgesia is not always applicable. Thus, there is a demand for analgesics that are well tolerated, have no or only few side effects, and may be administered to subjects with impaired hepatic or renal function even without the need for dose adaptation.

It is an object of the invention to provide improved pain therapy.

This object has been achieved by the subject-matter of the patent claims.

It has been unexpectedly found that Cebranopadol and its physiologically acceptable salts are very well tolerated and may be administered to subjects with hepatic and/or renal impairment, even without any change of treatment, particularly with respect to dosage, dosing frequency and administration regime, such that it may provide its full and complete therapeutic benefit.

The invention relates to Cebranopadol or a physiologically acceptable salt thereof for use in the treatment or the prevention of pain and/or opioid drug dependence in a subject with impaired hepatic and/or renal function. For the purpose of the invention, "impaired hepatic function" is synonymous to "hepatic impairment", whereas "impaired renal function" is synonymous to "renal impairment".

Cebranopadol (trans-6'-fluoro-4',9'-dihydro-N,N-dimethyl-4-phenyl-spiro[cyclohexane-1,1'-(3'H)-pyrano[3,4-b]indol]-4-amine) is an analgesic nociceptin/orphanin FQ peptide (NOP) and opioid receptor agonist (K. Linz et al., J Pharmacol Exp Ther. 2014, 349(3), 535-48; WO 2004/043967, WO 2006/108565, WO 2008/040481, WO 2012/016695, WO 2012/016697, WO 2012/016698, WO 2012/016699, WO 2012/016703, WO 2013/007361, WO 2013/087591, WO 2013/113690, WO 2013/113857, WO 2013/170965, WO 2013/170966, WO 2013/170967, WO 2013/170968, WO 2013/170969, WO 2013/170970, WO 2013/170971, WO 2013/170972).

Physiologically acceptable salts of Cebranopadol according to the invention include but are not limited to the hydrochloride salt and the salts with citric acid, particularly the hemicitrate. Preferably, Cebranopadol is administered as the free base.

According to the invention, the subjects have hepatic and/or renal impairment. Thus, the invention involves the prevention in or treatment of subjects having
 (i) impaired hepatic function but no impaired renal function;
 (ii) impaired renal function but no impaired hepatic function; or
 (iii) both, impaired hepatic function as well as impaired renal function.

Hepatic and renal function can be easily assessed by a skilled person and are subject to routine analysis. A skilled person can easily and clearly distinguish a subject having impaired hepatic function and/or impaired renal function from a subject having no impaired hepatic function and no impaired renal function, respectively.

The degree of the impairment of the hepatic function of the subject may be mild, moderate or severe. Preferably, the impairment of the hepatic function is at least mild, or at least moderate, or severe. In this regard, "at least mild" encompasses mild, moderate and severe, whereas "at least moderate" encompasses moderate and severe.

In a preferred embodiment, the impairment of the hepatic function is according to the Child-Pugh Score such that depending upon the degree of hepatic impairment the subjects may be classified in any one of classes A (mild), B (moderate) or C (severe) according to the Child-Pugh Score:

| Assessment | Degree of abnormality | Score |
|---|---|---|
| Encephalopathy | None | 1 |
|  | Moderate | 2 |
|  | Severe | 3 |
| Ascites | Absent | 1 |
|  | Slight | 2 |
|  | Moderate | 3 |
| Bilirubin [mg/dL] | <2 | 1 |
|  | 2.1 to 3 | 2 |
|  | >3 | 3 |
| Albumin | >3.5 | 1 |

| | | |
|---|---|---|
| [g/dL] | 2.8 to 3.5 | 2 |
|  | <2.8 | 3 |
| Prothrombin Time [seconds > control] | 0 to 3.9 | 1 |
|  | 4 to 6 | 2 |
|  | >6 | 3 |

| Total Score | Class | Severity |
|---|---|---|
| 5 to 6 | A | Mild |
| 7 to 9 | B | Moderate |
| 10 to 15 | C | Severe |

This categorization according to the Child-Pugh classification is in line with the respective EMA Guideline (*Guideline on the evaluation of the pharmacokinetics of medicinal products in subjects with impaired hepatic function*, 17 Feb. 2005, CPMP/EWP/2339/02) and FDA Guidance (*Guidance for Industry—Pharmacokinetics in subjects with impaired hepatic function: Study design, data analysis, and impact on dosing and labeling*, May 2003).

As mentioned above, hepatic impairment may be described qualitatively and quantitatively by various classification systems. Preferably, no dose adaptation is required when administering Cebranopadol to subjects across the full range of hepatic impairment according to the invention such that the classification system used is not relevant.

Preferably, the impairment of the hepatic function of the subject is of class A, B or C according to the Child-Pugh Score.

In preferred embodiments, the subject is classified by a total score according to the Child-Pugh classification of at least 5, or at least 6, or at least 7, or at least 8, or at least 9, or at least 10, or at least 11, or at least 12, or at least 13, or at least 14, or 15.

The causes of the impaired hepatic function are not particularly limited and include genetic disposition (e.g. inborn metabolic disorders and the like), acquired liver disease (e.g. diseases due to infection such as hepatitis, due to toxic substances such as alcohol, steatohepatosis, and the like), or side effect of a medication that is administered for treating another primary disorder or disease (e.g. chemotherapy, NSAIDs, and the like).

The degree of the impairment of the renal function of the subject may be mild, moderate or severe. Preferably, the impairment of the renal function, preferably in terms of decrease in estimated glomerular filtration rate (eGFR), is at least mild, or at least moderate, or severe. In this regard, "at least mild" encompasses mild, moderate and severe, whereas "at least moderate" encompasses moderate and severe.

As mentioned above, renal impairment may be described qualitatively and quantitatively by various classification systems. Preferably, no dose adaptation is required when administering Cebranopadol to subjects across the full range of renal impairment according to the invention such that the classification system used is not relevant.

In a preferred embodiment, the impairment of the renal function is based on the estimated creatinine clearance ($Cl_{CR}$) by the Cockcroft-Gault equation or on the estimated glomerular filtration rate (eGFR) from the Modification of Diet in Renal Disease (MDRD). Cockcrof-Gault and eGFR are two commonly used serum-creatinine based equations. Depending upon the degree of renal impairment the subjects may be classified in any one of stage 1 (normal), stage 2 (mild), stage 3 (moderate), stage 4 (severe) or stage 5 (end stage renal disease) according to the following classification of renal function based on eGFR or $CL_{Cr}$:

| Stage | Description | eGFR [mL/min/1.73 m²] | $CL_{Cr}$ [mL/min] |
|---|---|---|---|
| 1 | Normal GFR | ≥90 | ≥90 |
| 2 | Mild decrease in GFR | 60 to 89 | 60 to 89 |
| 3 | Moderate decrease in GFR | 30 to 59 | 30 to 59 |
| 4 | Severe decrease in GFR | 15 to 29 | 15 to 29 |
| 5 | End Stage Renal Disease (ESRD) | <15 not on dialysis requiring dialysis | <15 not on dialysis requiring dialysis |

This categorization according to eGFR or $CL_{Cr}$ is in line with the respective FDA Guidance (*Guidance for Industry—Pharmacokinetics in subjects with impaired renal function: Study design, data analysis, and impact on dosing and labeling*, draft guidance, March 2010, Revision 1). According to the invention different threshold values for mild, moderate and severe impairment of renal function may apply to specific subgroups of subjects, e.g. in pediatric subjects. These different threshold values are known to the skilled person and preferably are in accordance with the current FDA Guidance.

Preferably, the impairment of the renal function of the subject is of stage 2, 3 or 4 according to the estimated glomerular filtration rate eGFR or the creatinine clearance $Cl_{Cr}$.

In preferred embodiments, the subject is classified by an eGFR and a $CL_{Cr}$, respectively, of less than 90, or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, in either case mL/min/1.73 m² and mL/min, respectively.

The causes of the impaired renal function are not particularly limited and include genetic disposition, acquired kidney disease (e.g. chronic kidney disease, due to diabetes, arterial hypertension, infection), or side effect of a medication that is administered for treating another primary disorder or disease (e.g. chemotherapy, NSAIDs).

According to the invention, pain and/or opioid drug dependence are treated or prevented.

When pain is to be treated or prevented, the pain is preferably moderate, moderate to severe, or severe. The pain may be chronic or acute; and/or central and/or peripheral; and/or neuropathic and/or nociceptive. In connection with central/peripheral pain and with nociceptive/neuropathic pain "and/or" reflects the possibility that the overall pain may have different components, e.g. a nociceptive component as well as a neuropathic component. Preferably, the pain is chronic neuropathic pain, which may be peripheral or central; acute neuropathic pain, which may be peripheral or central; chronic nociceptive pain, which may be peripheral or central; or acute nociceptive pain, which may be peripheral or central.

Nociceptive pain refers to the discomfort that results when a stimulus causes tissue damage to the muscles, bones, skin or internal organs. For the purpose of the specification, nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). Nociceptive pain may also be divided into "visceral," "deep somatic" and "superficial somatic" pain.

Visceral pain describes a type of nociceptive pain originating in the body's internal organs or their surrounding tissues. This form of pain usually results from the infiltration of harmful cells, as well as the compression or extension of healthy cells. Subjects suffering from visceral pain tend to feel generally achy, as this pain tends to not be localized to a specific area. Cancer is a common source of visceral pain.

Somatic pain is nociceptive pain that results from some injury to the body. It's generally localized to the affected area and abates when the body repairs the damage to that area. Deep somatic pain is initiated by stimulation of nociceptors in ligaments, tendons, bones, blood vessels, fasciae and muscles, and is dull, aching, poorly-localized pain. Examples include sprains and broken bones. Superficial pain is initiated by activation of nociceptors in the skin or superficial tissues, and is sharp, well-defined and clearly located.

According to the invention, pain is preferably classified as chronic if it has occurred for at least 3 months or extends beyond the time of healing. Preferably, the chronic nociceptive pain is selected from chronic visceral pain, chronic deep somatic pain and chronic superficial somatic pain.

Preferred causes of nociceptive pain according to the invention include broken or fractured bones, bruises, burns, cuts, inflammation (from infection or arthritis), and sprains. Thus, nociceptive pain includes post-operative pain, cancer pain, low back pain, pain due to radiculopathy, and inflammatory pain.

Neuropathic pain is pain that originates from nerve damage or nerve malfunction. Preferably, the neuropathic pain is selected from acute neuropathic pain and chronic neuropathic pain. Neuropathic pain may be caused by damage or disease affecting the central or peripheral portions of the nervous system involved in bodily feelings (the somatosensory system). Preferably, the dosage form according to the invention is for use in the treatment of chronic neuropathic pain or acute neuropathic pain, peripheral neuropathic pain or central neuropathic pain, mononeuropathic pain or polyneuropathic pain. When the neuropathic pain is chronic, it may be chronic peripheral neuropathic pain or chronic central neuropathic pain, in a preferred embodiment chronic peripheral mononeuropathic pain or chronic central mononeuropathic pain, in another preferred embodiment chronic peripheral polyneuropathic pain or chronic central polyneuropathic pain. When the neuropathic pain is acute, it may be acute peripheral neuropathic pain or acute central neuropathic pain, in a preferred embodiment acute peripheral mononeuropathic pain or acute central mononeuropathic pain, in another preferred embodiment acute peripheral polyneuropathic pain or acute central polyneuropathic pain.

Central neuropathic pain is found in spinal cord injury, multiple sclerosis, and some strokes. Fibromyalgia is potentially a central pain disorder and is responsive to medications that are effective for neuropathic pain. Aside from diabetic neuropathy and other metabolic conditions, the common causes of painful peripheral neuropathies are herpes zoster infection, HIV-related neuropathies, nutritional deficiencies, toxins, remote manifestations of malignancies, genetic, and immune mediated disorders or physical trauma to a nerve trunk (e.g. due to disorders from the spinal disc, joint degeneration, or compression fracture). Neuropathic pain is common in cancer as a direct result of cancer on peripheral nerves (e.g., compression by a tumor), or as a side effect of chemotherapy, radiation injury or surgery.

In preferred embodiments, the pain is selected from postoperative pain, pain due to bunionectomy, visceral pain, cancer pain, pain due to diabetic polyneuropathy, pain due to osteoarthritis, fibromyalgia, low back pain, pain radiating down the lower limbs, pain due to (cervical or lumbar) radiculopathy, and inflammatory pain.

In preferred embodiments, the pain is selected from the group consisting of pain being or being associated with panic disorder [episodic paroxysmal anxiety] [F41.0]; dissociative [conversion] disorders [F44]; persistent somatoform pain disorder [F45.4]; pain disorders exclusively related to psychological factors [F45.41]; nonorganic dyspareunia [F52.6]; other enduring personality changes [F62.8]; sadomasochism [F65.5]; elaboration of physical symptoms for psychological reasons [F68.0]; migraine [G43]; other headache syndromes [G44]; trigeminal neuralgia [G50.0]; atypical facial pain [G50.1]; phantom limb syndrome with pain [G54.6]; phantom limb syndrome without pain [G54.7]; acute and chronic pain, not elsewhere classified [G89]; ocular pain [H57.1]; otalgia [H92.0]; angina pectoris, unspecified [120.9]; other specified disorders of nose and nasal sinuses [J34.8]; other diseases of pharynx [J39.2]; temporomandibular joint disorders [K07.6]; other specified disorders of teeth and supporting structures [K08.8]; other specified diseases of jaws [K10.8]; other and unspecified lesions of oral mucosa [K13.7]; glossodynia [K14.6]; other specified diseases of anus and rectum [K62.8]; pain in joint [M25.5]; shoulder pain [M25.51]; sacrococcygeal disorders, not elsewhere classified [M53.3]; spine pain [M54.]; radiculopathy [M54.1]; cervicalgia [M54.2]; sciatica [M54.3]; low back pain [M54.5]; pain in thoracic spine [M54.6]; other dorsalgia [M54.8]; dorsalgia, unspecified [M54.9]; other shoulder lesions [M75.8]; other soft tissue disorders, not elsewhere classified [M79]; myalgia [M79.1]; neuralgia and neuritis, unspecified [M79.2]; pain in limb [M79.6]; other specified disorders of bone [M89.8]; unspecified renal colic [N23]; other specified disorders of penis [N48.8]; other specified disorders of male genital organs [N50.8]; mastodynia [N64.4]; pain and other conditions associated with female genital organs and menstrual cycle [N94]; mittelschmerz [N94.0]; other specified conditions associated with female genital organs and menstrual cycle [N94.8]; pain in throat and chest [R07]; pain in throat [R07.0]; chest pain on breathing [R07.1]; precordial pain [R07.2]; other chest pain [R07.3]; chest pain, unspecified [R07.4]; abdominal and pelvic pain [R10]; acute abdomen pain [R10.0]; pain localized to upper abdomen [R10.1]; pelvic and perineal pain [R10.2]; pain localized to other parts of lower abdomen [R10.3]; other and unspecified abdominal pain [R10.4]; flatulence and related conditions [R14]; abdominal rigidity [R19.3]; other and unspecified disturbances of skin sensation [R20.8]; pain associated with micturition [R30]; other and unspecified symptoms and signs involving the urinary system [R39.8]; headache [R51]; pain, not elsewhere classified [R52]; acute pain [R52.0]; chronic intractable pain [R52.1]; other chronic pain [R52.2]; pain, unspecified [R52.9]; other complications of cardiac and vascular prosthetic devices, implants and grafts [T82.8]; other complications of genitourinary prosthetic devices, implants and grafts [T83.8]; other complications of internal orthopaedic prosthetic devices, implants and grafts [T84.8]; other complications of internal prosthetic devices, implants and grafts, not elsewhere classified [T85.8]; wherein the information in brackets refers to the classification according to ICD-10.

The dose of Cebranopadol or of the physiologically acceptable salt thereof that is administered to the subject is not particularly limited, as it has been unexpectedly found that Cebranopadol is so well tolerated that it may even be administered to subjects with impaired hepatic function and/or impaired renal function without any change of treatment, particularly with respect to dosage, dosing frequency and administration regime.

Thus, Cebranopadol or the physiologically acceptable salt thereof is preferably administered at a dose that would also be administered to a subject in the same condition but without impaired hepatic and/or without impaired renal function.

Depending upon the type and degree of pain to be treated or prevented, Cebranopadol or the physiologically acceptable salt thereof is administered at a dose that in the subject's perception results in an amelioration of pain at acceptable side effects. Typically, the dose is within the range of from 20 µg to 2000 µg, as equivalent dose relative to Cebranopadol free base. As Cebranopadol or the physiologically acceptable salt thereof is preferably administered once daily, this dose preferably corresponds to the daily dose.

In preferred embodiments, Cebranopadol or the physiologically acceptable salt thereof is administered at a dose of at least 20 µg, at least 25 µg, at least 30 µg, at least 40 µg, at least 50 µg, at least 60 µg, at least 70 µg, at least 75 µg, at least 80 µg, at least 90 µg, at least 100 µg, at least 125 µg, at least 150 µg, at least 175 µg, at least 200 µg, at least 225 µg, at least 250 µg, at least 275 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1000 µg, at least 1100 µg, at least 1200 µg, at least 1300 µg, at least 1400 µg, at least 1500 µg, at least 1600 µg, at least 1700 µmg, at least 1800 µg, at least 1900 µg, or at least 2000 µg, as equivalent dose relative to Cebranopadol free base.

In preferred embodiments, Cebranopadol or the physiologically acceptable salt thereof is administered at a dose within the range of 50±30 µg, 50±25 µg, 75±25 µg, 100±25 µg, 150±50 µg, 200±50 µg, 250±50 µg, 300±50 µg, 350±50 µg, 400±50 µg, 450±50 µg, 500±50 µg, 600±100 µg, 700±100 µg, 750±100 µg, 800±100 µg, 900±100 µg, 1000±100 µg, 1100±100 µg, 1200±100 µg, 1300±100 µg, 1400±100 µg, 1500±100 µg, 1600±100 µg, 1700±100 µg, 1800±100 µg, 1900±100 µg, or 2000±100 µg, as equivalent dose relative to Cebranopadol free base.

In preferred embodiment, particularly when pain is to be treated or prevented, Cebranopadol or the physiologically acceptable salt thereof is preferably administered orally once daily at a dose within the range of from 20 µg to 2000 µg, or from 25 µg to 2000 µg, or from 40 µg to 2000 µg, or from 80 µg to 2000 µg, or from 100 µg to 2000 µg, or from 200 µg to 2000 µg, or from 300 µg to 2000 µg, or from 400 µg to 2000 µg, or from 500 µg to 2000 µg, or from 600 µg to 2000 µg, or from 20 µg to 1600 µg, or from 25 µg to 1600 µg, or from 40 µg to 1600 µg, or from 80 µg to 1600 µg, or from 100 µg to 1600 µg, or from 200 µg to 1600 µg, or from 300 µg to 1600 µg, or from 400 µg to 1600 µg, or from 500 µg to 1600 µg, or from 600 µg to 1600 µg, or from 40 µg to 2000 µg, or from 40 µg to 1600 µg, or from 40 µg to 1200 µg, or from 40 µg to 1000 µg, or from 40 µg to 800 µg, or from 80 µg to 2000 µg, or from 80 µg to 1600 µg, or from 80 µg to 1200 µg, or from 80 µg to 1000 µg, or from 80 µg to 800 µg, or from 100 µg to 2000 µg, or from 100 µg to 1600 µg, or from 100 µg to 1200 µg, or from 100 µg to 1000 µg, or from 100 µg to 800 µg, or from 200 µg to 2000 µg, or from 200 µg to 1600 µg, or from 200 µg to 1200 µg, or from 200 µg to 1000 µg, or from 200 µg to 800 µg, or from 300 µg to 2000 µg, or from 300 µg to 1600 µg, or from 300 µg to 1200 µg, or from 300 µg to 1000 µg, or from 300 µg to 800 µg, or from 400 µg to 2000 µg, or from 400 µg to 1600 µg, or from 400 µg to 1200 µg, or from 400 µg to 1000 µg, or from 400 µg to 800 µg, as equivalent dose relative to Cebranopadol free base.

In preferred embodiments, particularly when opioid drug dependence is to be treated or prevented, Cebranopadol or the physiologically acceptable salt thereof is preferably administered orally once daily at a dose within the range of from 20 µg to 2000 µg, or 40 µg to 2000 µg, or from 80 µg to 2000 µg, or from 100 µg to 2000 µg, or from 200 µg to 2000 µg, or from 300 µg to 2000 µg, or from 400 µg to 2000 µg, or from 500 µg to 2000 µg, or from 600 µg to 2000 µg, or from 40 µg to 1600 µg, or from 80 µg to 1600 µg, or from 100 µg to 1600 µg, or from 200 µg to 1600 µg, or from 300 µg to 1600 µg, or from 400 µg to 1600 µg, or from 500 µg to 1600 µg, or from 600 µg to 1600 µg, or from 40 µg to 2000 µg, or from 40 µg to 1600 µg, or from 40 µg to 1200 µg, or from 40 µg to 1000 µg, or from 40 µg to 800 µg, or from 80 µg to 2000 µg, or from 80 µg to 1600 µg, or from 80 µg to 1200 µg, or from 80 µg to 1000 µg, or from 80 µg to 800 µg, or from 100 µg to 2000 µg, or from 100 µg to 1600 µg, or from 100 µg to 1200 µg, or from 100 µg to 1000 µg, or from 100 µg to 800 µg, or from 200 µg to 2000 µg, or from 200 µg to 1600 µg, or from 200 µg to 1200 µg, or from 200 µg to 1000 µg, or from 200 µg to 800 µg, or from 300 µg to 2000 µg, or from 300 µg to 1600 µg, or from 300 µg to 1200 µg, or from 300 µg to 1000 µg, or from 300 µg to 800 µg, or from 400 µg to 2000 µg, or from 400 µg to 1600 µg, or from 400 µg to 1200 µg, or from 400 µg to 1000 µg, or from 400 µg to 800 µg, as equivalent dose relative to Cebranopadol free base.

Preferably, Cebranopadol or the physiologically acceptable salt thereof is administered systemically, more preferably orally.

Preferably, Cebranopadol or the physiologically acceptable salt thereof is administered once daily.

When the pain to be treated or prevented is chronic neuropathic pain, Cebranopadol or the physiologically acceptable salt thereof is preferably administered orally once daily at a dose of at least 20 µg, at least 25 µg, at least 30 µg, at least 40 µg, at least 50 µg, at least 60 µg, at least 70 µg, at least 75 µg, at least 80 µg, at least 90 µg, at least 100 µg, at least 125 µg, at least 150 µg, at least 175 µg, at least 200 µg, at least 225 µg, or at least 250 µg, at least 275 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1000 µg, at least 1100 µg, at least 1200 µg, at least 1300 µg, at least 1400 µg, at least 1500 µg, at least 1600 µg, at least 1700 µmg, at least 1800 µg, at least 1900 µg, or at least 2000 µg, as equivalent dose relative to Cebranopadol free base.

When the pain to be treated or prevented is acute neuropathic pain, Cebranopadol or the physiologically acceptable salt thereof is preferably administered orally once daily at a dose of at least 20 µg, at least 25 µg, at least 30 µg, at least 40 µg, at least 50 µg, at least 60 µg, at least 70 µg, at least 75 µg, at least 80 µg, at least 90 µg, at least 100 µg, at least 125 µg, at least 150 µg, at least 175 µg, at least 200 µg, at least 225 µg, or at least 250 µg, at least 275 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1000 µg, at least 1100 µg, at least 1200 µg, at least 1300 µg, at least 1400 µg, at least 1500 µg, at least 1600 µg, at least 1700 µmg, at least 1800 µg, at least 1900 µg, or at least 2000 µg, as equivalent dose relative to Cebranopadol free base.

When the pain to be treated or prevented is chronic nociceptive pain, Cebranopadol or the physiologically acceptable salt thereof is preferably administered orally once daily at a dose of at least 40 µg, at least 50 µg, at least 60 µg, at least 70 µg, at least 75 µg, at least 80 µg, at least 90 µg, at least 100 µg, at least 125 µg, at least 150 µg, at least 175 µg, at least 200 µg, at least 225 µg, or at least 250 µg, at least 275 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1000 µg, at least 1100 µg, at least 1200 µg, at least 1300 µg, at least 1400 µg, at least 1500 µg, at least 1600 µg, at least 1700 µmg, at least 1800 µg, at least 1900 µg, or at least 2000 µg, as equivalent dose relative to Cebranopadol free base.

When the pain to be treated or prevented is acute nociceptive pain, Cebranopadol or the physiologically acceptable salt thereof is preferably administered orally once daily at a dose of at least 80 µg, at least 90 µg, at least 100 µg, at least 125 µg, at least 150 µg, at least 175 µg, at least 200 µg, at least 225 µg, or at least 250 µg, at least 275 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1000 µg, at least 1100 µg, at least 1200 µg, at least 1300 µg, at least 1400 µg, at least 1500 µg, at least 1600 µg, at least 1700 µmg, at least 1800 µg, at least 1900 µg, or at least 2000 µg, as equivalent dose relative to Cebranopadol free base.

When opioid drug dependence is to be treated or prevented, Cebranopadol or the physiologically acceptable salt thereof is preferably administered orally once daily at a dose of at least 40 µg, at least 50 µg, at least 60 µg, at least 70 µg, at least 75 µg, at least 80 µg, at least 90 µg, at least 100 µg, at least 125 µg, at least 150 µg, at least 175 µg, at least 200 µg, at least 225 µg, or at least 250 µg, at least 275 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1000 µg, at least 1100 µg, at least 1200 µg, at least 1300 µg, at least 1400 µg, at least 1500 µg, at least 1600 µg, at least 1700 µmg, at least 1800 µg, at least 1900 µg, or at least 2000 µg, as equivalent dose relative to Cebranopadol free base.

The duration of treatment is not particularly limited and may last for several weeks or months or years, especially when the pain to be treated or prevented is chronic. Preferably, when the pain is chronic, the pain is treated for at least one week or at least two weeks.

The age and gender of the subject is not particularly limited. Preferably, the subject is human, more preferably an adult or a child (pediatric).

Another aspect of the invention relates to the use of Cebranopadol or a physiologically acceptable salt thereof for the manufacture of a medicament for the treatment or the prevention of pain and/or opioid drug dependence in a subject with impaired hepatic and/or renal function.

Another aspect of the invention relates to a method for the treatment or the prevention of pain and/or opioid drug dependence comprising the administration of a therapeutically effective amount of Cebranopadol or a physiologically acceptable salt thereof to a subject with impaired hepatic and/or renal function.

All preferred embodiments that have been described above in connection with Cebranopadol or the physiologically acceptable salt thereof for use in the treatment or the prevention of pain and/or opioid drug dependence according to the invention also analogously apply to the use of Cebranopadol or a physiologically acceptable salt thereof for the manufacture of a medicament according to the invention and to the method for the treatment or the prevention of pain and/or opioid drug dependence according to the invention.

The following examples further illustrate the invention but are not to be construed as limiting its scope:

EXAMPLE 1—HEPATIC IMPAIRMENT AT A DOSE OF 200 μg

In a Phase I single dose, open label study with 200 μg Cebranopadol the pharmacokinetics and safety of Cebranopadol in healthy subjects with normal hepatic function and subjects with impaired hepatic function was investigated. 32 subjects completed the study, 8 subjects with normal hepatic function, 8 subjects with mildly impaired hepatic function, 8 subjects with moderately impaired hepatic function, and 8 subjects with severely impaired hepatic function (Child-Pugh score).

Pharmacokinetic data for Cebranopadol as well as for M2, M3 and M6 metabolite are summarized in the following table (rounded values):

| | | | | | $T_{max}$ [h] | $C_{max}$ [pg/mL] | $AUC_{0-t}$ [h · pg/mL] | $AUC_{0-\infty}$ [h · pg/mL] |
|---|---|---|---|---|---|---|---|---|
| Cebranopadol | hepatic impairment | Mild | N | | 8 | 8 | 8 | 8 |
| | | | Mean | | 5.5 | 74 | 1564 | 1912 |
| | | | SD | | 1.2 | 29 | 582 | 705 |
| | | Moderate | N | | 8 | 8 | 8 | 8 |
| | | | Mean | | 4.8 | 95 | 2380 | 3255 |
| | | | SD | | 2.1 | 36 | 903 | 1208 |
| | | Severe | N | | 8 | 8 | 8 | 8 |
| | | | Mean | | 2.9 | 91 | 1962 | 2863 |
| | | | SD | | 1.5 | 26 | 640 | 1246 |
| | | None | N | | 8 | 8 | 8 | 8 |
| | | | Mean | | 5.8 | 81 | 1700 | 2056 |
| | | | SD | | 2.0 | 32 | 495 | 579 |
| M2 metabolite | | Mild | N | | 8 | 8 | 8 | 8 |
| | | | Mean | | 11.6 | 7.1 | 461 | 785 |
| | | | SD | | 10.3 | 4.6 | 259 | 406 |
| | | Moderate | N | | 8 | 8 | 8 | 8 |
| | | | Mean | | 18.8 | 4.9 | 389 | 1014 |
| | | | SD | | 15.8 | 2.6 | 212 | 503 |
| | | Severe | N | | 8 | 8 | 8 | 8 |
| | | | Mean | | 20.0 | 4.0 | 358 | 1249 |
| | | | SD | | 14.6 | 2.9 | 211 | 929 |
| | | None | N | | 8 | 8 | 8 | 8 |
| | | | Mean | | 10.3 | 7.7 | 523 | 953 |
| | | | SD | | 6.4 | 2.2 | 111 | 379 |
| M3 metabolite | | Mild | N | | 8 | 8 | 8 | 8 |
| | | | Mean | | 8.1 | 10.7 | 481 | 732 |
| | | | SD | | 2.9 | 3.4 | 221 | 391 |
| | | Moderate | N | | 8 | 8 | 8 | 8 |
| | | | Mean | | 7.4 | 10.0 | 548 | 930 |
| | | | SD | | 3.0 | 4.7 | 234 | 481 |
| | | Severe | N | | 8 | 8 | 8 | 7 |
| | | | Mean | | 20.5 | 9.6 | 588 | 1076 |
| | | | SD | | 32.4 | 3.0 | 259 | 621 |
| | | None | N | | 8 | 8 | 8 | 8 |
| | | | Mean | | 8.0 | 8.0 | 306 | 374 |
| | | | SD | | 2.8 | 2.9 | 116 | 147 |
| M6 metabolite | | Mild | N | | 8 | 8 | 8 | 7 |
| | | | Mean | | 13.8 | 14.2 | 981 | 2707 |
| | | | SD | | 9.3 | 6.4 | 423 | 1412 |
| | | Moderate | N | | 8 | 8 | 8 | 4 |
| | | | Mean | | 67.5 | 7.2 | 603 | 1911 |
| | | | SD | | 50.5 | 3.1 | 195 | 1127 |
| | | Severe | N | | 8 | 8 | 8 | 2 |
| | | | Mean | | 70.3 | 4.3 | 369 | 2272 |
| | | | SD | | 40.7 | 2.6 | 173 | 2615 |
| | | None | N | | 8 | 8 | 8 | 8 |
| | | | Mean | | 13.9 | 11.2 | 769 | 1855 |
| | | | SD | | 10.8 | 4.2 | 255 | 882 |

Common treatment emergent adverse events (≥2 subjects) are summarized in the following table:

| | hepatic impairment | | | |
|---|---|---|---|---|
| no of subjects | mild | moderate | severe | none |
| at least one treatment emergent adverse event | 2 | 4 | 4 | 2 |

-continued

| no of subjects | hepatic impairment | | | |
|---|---|---|---|---|
| | mild | moderate | severe | none |
| headache | 2 | 1 | 1 | 1 |
| nausea | 0 | 1 | 1 | 0 |

Neither serious adverse events nor deaths were observed during the trial. No subject discontinued the trial due to treatment emergent adverse events. The most common treatment emergent adverse events were headache and nausea. The profile of treatment emergent adverse events was similar across all hepatic function groups. Based on the safety data evaluation of this trial, there were no unexpected safety findings.

The above findings indicate that Cebranopadol is well tolerated and can be administered to subjects with hepatic impairment without adjustment of dose.

EXAMPLE 2—RENAL IMPAIRMENT AT A DOSE OF 200 µg (PRELIMINARY AND FINAL DATA)

In a Phase I single dose, open label study with 200 µg Cebranopadol the pharmacokinetics and safety of Cebranopadol in subjects with different degrees of impaired renal function was investigated.

8 healthy subjects, 8 subjects with mildly impaired renal function, 9 subjects with moderately impaired renal function, and 8 subjects with severely impaired renal function (decrease in GFR, estimated glomerular filtration rate (eGFR) from the Modification of Diet in Renal Disease (MDRD)) completed the trial and received a single oral 200 µg dose of Cebranopadol (final data).

Preliminary and final pharmacokinetic data for Cebranopadol as well as for M2, M3 and M6 metabolite are summarized in the following table (rounded values):

| | | | | Preliminary data | | Final data | | | |
|---|---|---|---|---|---|---|---|---|---|
| | | | | $C_{max}$ [pg/mL] | $AUC_{last}$ [h · pg/mL] | $T_{max}$ [h] | $C_{max}$ [pg/mL] | $AUC_{0-t}$ [h · pg/mL] | $AUC_{0-\infty}$ [h · pg/mL] |
| Cebranopadol | renal impairment | Mild | N | 8 | 8 | N | 9 | 9 | 6 |
| | | | Mean | 144 | 3180 | Mean | 5.2 | 144 | 3132 | 3229 |
| | | | SD | 65.3 | 1350 | SD | 3.2 | 65.3 | 1407 | 1748 |
| | | Moderate | N | 8 | 8 | N | 8 | 8 | 8 | 7 |
| | | | Mean | 128 | 3120 | Mean | 4.6 | 128 | 3122 | 3893 |
| | | | SD | 41.8 | 1490 | SD | 0.9 | 41.8 | 1488 | 1949 |
| | | Severe | N | 8 | 8 | N | 8 | 8 | 8 | 4 |
| | | | Mean | 131 | 2950 | Mean | 5.3 | 131 | 2946 | 3533 |
| | | | SD | 28.2 | 775 | SD | 2.0 | 28.2 | 775 | 1131 |
| | | None | N | 8 | 8 | N | 8 | 8 | 8 | 5 |
| | | | Mean | 125 | 2650 | Mean | 4.4 | 125 | 2650 | 2728 |
| | | | SD | 67.9 | 1360 | SD | 1.3 | 67.9 | 1358 | 1086 |
| M2 metabolite | | Mild | N | 8 | 8 | N | 9 | 9 | 9 | 1 |
| | | | Mean | 13.1 | 1140 | Mean | 10.2 | 13.2 | 1078 | 1030 |
| | | | SD | 6.89 | 572 | SD | 5.9 | 6.89 | 608 | |
| | | Moderate | N | 8 | 8 | N | 8 | 8 | 8 | 2 |
| | | | Mean | 8.97 | 782 | Mean | 11.3 | 8.97 | 782 | 885 |
| | | | SD | 4.86 | 490 | SD | 5.7 | 4.86 | 490 | 11 |
| | | Severe | N | 8 | 8 | N | 8 | 8 | 8 | 1 |
| | | | Mean | 6.39 | 600 | Mean | 12.5 | 6.39 | 600 | 912 |
| | | | SD | 3.45 | 306 | SD | 9.7 | 3.45 | 306 | |
| | | None | N | 8 | 8 | N | 8 | 8 | 8 | 1 |
| | | | Mean | 8.31 | 699 | Mean | 9.0 | 8.31 | 699 | 744 |
| | | | SD | 2.81 | 233 | SD | 1.1 | 2.81 | 233 | |
| M3 metabolite | | Mild | N | 8 | 8 | N | 9 | 9 | 9 | 4 |
| | | | Mean | 10.1 | 624 | Mean | 7.7 | 10.1 | 608 | 514 |
| | | | SD | 8.62 | 920 | SD | 2.6 | 8.63 | 926 | 369 |
| | | Moderate | N | 8 | 8 | N | 8 | 8 | 8 | 5 |
| | | | Mean | 7.93 | 423 | Mean | 9.5 | 7.93 | 423 | 352 |
| | | | SD | 3.24 | 262 | SD | 2.6 | 3.24 | 262 | 178 |
| | | Severe | N | 8 | 8 | N | 8 | 8 | 8 | 5 |
| | | | Mean | 9.08 | 580 | Mean | 12.0 | 9.08 | 580 | 503 |
| | | | SD | 6.22 | 484 | SD | 9.9 | 6.22 | 484 | 340 |
| | | None | N | 8 | 8 | N | 8 | 8 | 8 | 3 |
| | | | Mean | 8.65 | 438 | Mean | 7.9 | 8.65 | 438 | 309 |
| | | | SD | 6.23 | 453 | SD | 2.3 | 6.23 | 453 | 53 |
| M6 metabolite | | Mild | N | 8 | 8 | N | 8 | 8 | 8 | 0 |
| | | | Mean | 14.0 | 1350 | Mean | 16.8 | 14.02 | 1232 | |
| | | | SD | 2.99 | 462 | SD | 10.3 | 2.99 | 465 | |
| | | Moderate | N | 8 | 8 | N | 8 | 8 | 8 | 0 |
| | | | Mean | 10.4 | 1110 | Mean | 29.5 | 10.36 | 1112 | |
| | | | SD | 2.22 | 228 | SD | 10.2 | 2.22 | 228 | |
| | | Severe | N | 8 | 8 | N | 8 | 8 | 8 | 1 |
| | | | Mean | 7.87 | 902 | Mean | 54.5 | 7.87 | 902 | 1132 |
| | | | SD | 3.73 | 415 | SD | 70.7 | 3.73 | 415 | |
| | | None | N | 8 | 8 | N | 8 | 8 | 8 | 0 |
| | | | Mean | 10.4 | 1040 | Mean | 34.5 | 10.40 | 1038 | |
| | | | SD | 2.40 | 209 | SD | 33.4 | 2.40 | 209 | |

It can be concluded from the above data that there was no indication for any trend in main pharmacokinetic parameters for Cebranopadol or its metabolites M2, M3 and M6 with increasing degree of renal impairment. The highest mean exposure was observed for the subjects in the mild impairment group.

14 out of 33 subjects (42.4%) reported as total 30 adverse events (preliminary data):

|  | Renal impairment | | | |
|---|---|---|---|---|
|  | Mild N = 8 | Moderate N = 9 | Severe N = 8 | None N = 8 |
| subjects with adverse events | 5 (62.5%) | 3 (33.3%) | 2 (25.0%) | 3 (37.5%) |
| number of events | 10 (33.3%) | 9 (30.0%) | 7 (23.3%) | 4 (13.3%) |

13 out of 34 subjects (38.2%) reported as total 30 adverse events (final data):

|  | Renal impairment | | | |
|---|---|---|---|---|
|  | Mild N = 9 | Moderate N = 9 | Severe N = 8 | None N = 8 |
| subjects with adverse events | 5 (55.6%) | 3 (33.3%) | 2 (25.0%) | 3 (37.5%) |
| number of events | 10 (33.3%) | 9 (30.0%) | 7 (23.3%) | 4 (13.3%) |

No deaths or serious adverse events were reported.

19 out of 30 adverse events (63.3%) were expected adverse events such as dizziness, nausea, vomiting, and fatigue. 11 out of 30 adverse events (36.7%) were unexpected (preliminary data):

|  | Renal impairment | | | | |
|---|---|---|---|---|---|
|  | Mild | Moderate | Severe | None | Total |
| increased blood pressure | 1 |  |  | 1 | 2 |
| headache |  | 2 |  | 1 | 3 |
| orbital pain |  | 1 |  |  | 1 |
| increased frequency of urination |  |  |  | 2 | 2 |
| low back pain | 2 |  |  |  | 2 |
| electrical shock/soft tissue injury |  |  | 1 |  | 1 |
| total | 3 | 3 | 1 | 4 | 11 |

All events were resolved. No severe adverse event was reported. 7 (preliminary data) or 6 (final data), respectively, moderate adverse events were reported. The majority of adverse events (except 3) were reported as related to Cebranopadol.

The above findings indicate that the use of single dose 200 μg Cebranopadol in subjects with different degrees of renal impairment was safe and well tolerated. The overall tolerability of Cebranopadol was not affected by the degree of renal impairment. No dose adjustment for Cebranopadol was considered necessary in subjects with impaired renal function.

EXAMPLE 3—RENAL IMPAIRMENT AT HIGHER DOSES

In a Phase IIb trial subjects with normal renal function, with mild impairment of renal function and with moderate impairment of renal function (decrease in GFR, calculated from the Cockcroft-Gault formula) were treated with Cebranopadol at oral doses of 200 μg, 400 μg and 600 μg, respectively. The occurrence of treatment emergent adverse events (TEAE) is summarized in the table below:

|  | Cebranopadol 200 μg | | Cebranopadol 400 μg | | Cebranopadol 600 μg | | Cebranopadol overall | | placebo | |
|---|---|---|---|---|---|---|---|---|---|---|
| No. of subjects | N | with TEAE | N | with TEAE | N | with TEAE | N | with TEAE | N | with TEAE |
| moderate | 5 | 5 (100%) | 1 | 1 (100%) | 2 | 2 (100%) | 8 | 8 (100%) | 4 | 2 (50.0%) |
| mild | 35 | 30 (85.7%) | 43 | 38 (88.4%) | 41 | 37 (90.2%) | 119 | 105 (88.2%) | 40 | 23 (57.5%) |
| normal | 90 | 73 (81.1%) | 83 | 68 (81.9%) | 85 | 76 (89.4%) | 258 | 217 (84.1%) | 82 | 57 (69.5%) |

All the subjects with moderate renal impairment had treatment emergent adverse events—100%. However, the numbers are very small so that a statistically relevant conclusion cannot be made. The subjects with mild renal impairment had similar overall frequencies of treatment emergent adverse events like the subjects with normal renal function.

Within the subjects with moderate renal impairment the reported treatment emergent adverse events are among the ones typically seen in Cebranopadol Phase II trials and include nausea, vomiting, dizziness, and somnolence. Single cases of other treatment emergent adverse events reported were as follows:

|  | Cebranopadol 200 µg N = 5 | Cebranopadol 400 µg N = 1 | Cebranopadol 600 µg N = 2 | overall N = 8 | placebo N = 4 |
|---|---|---|---|---|---|
| urinary tract infection | 1 | 0 | 0 | 1 | 0 |
| creatinine clearance decreased | 1 | 0 | 0 | 1 | 0 |
| disturbance attention | 0 | 0 | 1 | 1 | 0 |
| head discomfort | 1 | 0 | 0 | 1 | 0 |
| pre-renal failure | 0 | 0 | 1 | 1 | 0 |

2 treatment emergent adverse events were related to the underlying renal impairment, no treatment emergent adverse events occurred more than once and there was no pattern.

Within the subjects with mild renal impairment, the following treatment emergent adverse events were reported:

| [%] | overall, mild renal impairment N = 119 | overall, normal renal function N = 258 |
|---|---|---|
| constipation | 19.3 | 14.7 |
| dry mouth | 5.9 | 1.9 |
| nausea | 31.9 | 27.9 |
| vomiting | 21.0 | 16.3 |
| fatigue | 16.8 | 13.6 |
| dizziness | 31.9 | 37.6 |
| somnolence | 19.3 | 17.4 |
| hyperhidrosis | 5.0 | 12.0 |

Frequencies of treatment emergent adverse events were similar in subjects with mild renal impairment and normal renal function.

The above findings indicate that Cebranopadol is well tolerated. The administration of Cebranopadol multiple doses up to 600 µg/day was safe in subjects with mild and moderate renal impairment. No specific risk for subjects with mildly or moderately impaired renal function was identified.

The invention claimed is:

1. A method for treating or preventing pain and/or opioid drug dependence comprising administering Cebranopadol or a physiologically acceptable salt thereof to a subject in need thereof, wherein the subject has impaired hepatic and/or renal function.

2. The method for treating or preventing pain and/or opioid drug dependence according to claim 1, wherein
   the impairment of the hepatic function is mild, moderate or severe; and/or
   the impairment of the renal function is mild, moderate or severe.

3. The method for treating or preventing pain and/or opioid drug dependence according to claim 1, wherein
   the impairment of the hepatic function is of class A, B or C according to the Child-Pugh Score; and/or
   the impairment of the renal function is of stage 2, 3 or 4 according to the estimated glomerular filtration rate (eGFR) or according to the creatinine clearance (ClCr).

4. The method for treating or preventing pain and/or opioid drug dependence according to claim 1, wherein the pain is moderate, moderate to severe, or severe.

5. The method for treating or preventing pain and/or opioid drug dependence according to claim 1, wherein the pain is
   chronic or acute; and/or
   central and/or peripheral; and/or
   neuropathic and/or nociceptive.

6. The method for treating or preventing pain and/or opioid drug dependence according to claim 1, wherein the pain is selected from postoperative pain, pain due to bunionectomy, visceral pain, cancer pain, pain due to diabetic polyneuropathy, pain due to osteoarthritis, fibromyalgia, back pain, pain due to radiculopathy, pain radiating down the lower limbs, and inflammatory pain.

7. The method for treating or preventing pain and/or opioid drug dependence according to claim 1, wherein Cebranopadol or the physiologically acceptable salt thereof is administered at a dose that would also be administered to a subject in the same condition but without impaired hepatic and without impaired renal function.

8. The method for treating or preventing pain and/or opioid drug dependence according to claim 1, wherein Cebranopadol or the physiologically acceptable salt thereof is administered at a dose within the range of from 20 µg to 2000 µg, as equivalent dose relative to Cebranopadol free base.

9. The method for treating or preventing pain and/or opioid drug dependence according to claim 1, wherein Cebranopadol or the physiologically acceptable salt thereof is administered systemically.

10. The method for treating or preventing pain and/or opioid drug dependence according to claim 1, wherein Cebranopadol or the physiologically acceptable salt thereof is administered orally.

11. The method for treating or preventing pain and/or opioid drug dependence according to claim 1, wherein Cebranopadol or the physiologically acceptable salt thereof is administered once daily.

12. The method for treating or preventing pain and/or opioid drug dependence according to claim 1, wherein pain is treated for at least one week.

13. The method for treating or preventing pain and/or opioid drug dependence according to claim 1, wherein the subject is an adult or a pediatric subject.

14. The method for treating or preventing pain and/or opioid drug dependence according to claim 1, wherein pain is to be treated or prevented and
   the pain is chronic neuropathic pain and Cebranopadol or the physiologically acceptable salt thereof is administered orally once daily at a dose of at least 20 µg; or
   the pain is acute neuropathic pain and Cebranopadol or the physiologically acceptable salt thereof is administered orally once daily at a dose of at least 20 µg; or
   the pain is chronic nociceptive pain and Cebranopadol or the physiologically acceptable salt thereof is administered orally once daily at a dose of at least 40 µg; or
   the pain is acute nociceptive pain and Cebranopadol or the physiologically acceptable salt thereof is administered orally once daily at a dose of at least 80 µg;
   in each case as equivalent dose relative to Cebranopadol free base.

15. The method for treating or preventing pain and/or opioid drug dependence according to claim 1, wherein opioid drug dependence is to be treated or prevented and Cebranopadol or the physiologically acceptable salt thereof is administered orally once daily at a dose of at least 40 μg, as equivalent dose relative to Cebranopadol free base.

* * * * *